United States Patent [19]

Nader

[11] Patent Number: 5,410,083

[45] Date of Patent: Apr. 25, 1995

[54] SYNTHESIS OF DIAMINORESORCINAL FROM RESORCINOL

[75] Inventor: Bassam S. Nader, Midland, Mich.

[73] Assignee: The Dow Chemical Company, Midland, Mich.

[21] Appl. No.: 137,654

[22] Filed: Oct. 15, 1993

[51] Int. Cl.⁶ .......................................... C07C 209/36
[52] U.S. Cl. .................................... 564/418; 564/423; 568/765
[58] Field of Search ................ 568/765, 766; 564/443, 564/409, 418, 423

[56] References Cited

U.S. PATENT DOCUMENTS

| | | | |
|---|---|---|---|
| 2,023,160 | 12/1935 | Austin | 260/154 |
| 2,439,421 | 4/1948 | Erickson | 260/625 |
| 2,448,942 | 9/1948 | Winkler | 260/621 |
| 3,578,716 | 5/1971 | Robinson | 260/650 |
| 3,929,907 | 12/1975 | Janzon et al. | 260/619 R |
| 4,704,469 | 11/1987 | Valle | 560/65 |
| 4,766,244 | 8/1988 | Lysenko | 564/418 |
| 4,982,001 | 1/1991 | Lysenko et al. | 564/418 |

OTHER PUBLICATIONS

CA 114:228521 (Dec. 1991).
"Polybenzothiazoles and Polybenzoxazoles" listed in The Encyclopedia of Polymer Science and Engineering, vol. 11, pp. 601–635, ©1988 by John Wiley & Sons, Inc.
Friedel Crafts and Related Reactions, vol. II, Part I, p. 501, ©1964 by John Wiley & Sons Ltd.
"Condensation of Aliphatic Alcohols with Aromatic Compounds in the Presence of Aluminum Chloride" by R. C. Huston et al.; listed in J. Am. Chem. Soc., vol. 58, pp. 439–441 (1936).
Advanced Organic Chemistry, 2nd Ed. ©1977, McGraw-Hill Inc., pp. 964–967.
"Autocatalysis in Aromatic Alkylations. The Reaction of Phenols with Triphenylmethy Chloride" by Harold Hart et al.; listed in J. Am. Chem. Soc., vol. 76, pp. 1634–1639 (Mar. 1954).

Primary Examiner—Allen J. Robinson
Assistant Examiner—Brian M. Burn

[57] ABSTRACT

The invention relates to a novel process for preparing 4,6-diaminoresorcinol, a precursor to polybenzoxazole, from resorcinol according to the following scheme.

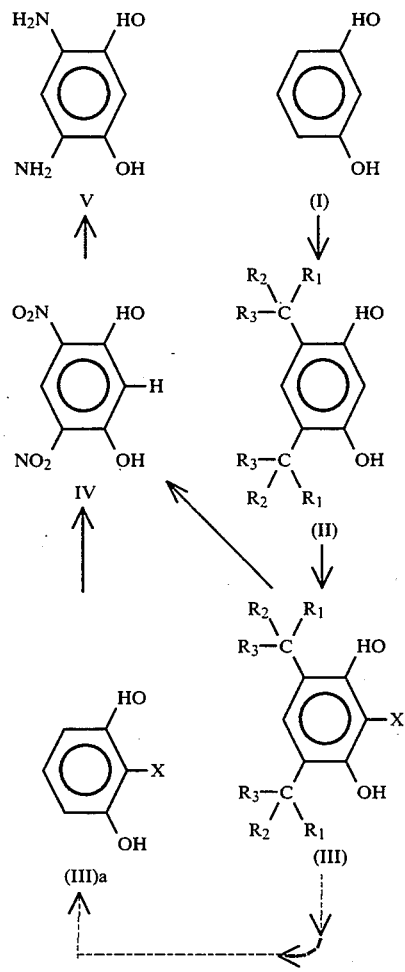

(Abstract continued on next page.)

Resorcinol (I) is reacted with a di-tert-alkylating reagent to form a 4,6,-di-tert-alkylresorcinol (II), which is then halogenated to form a 2-halo-4,6-di-tert-alkylresorcinol (III). The 2-halo-4,6-di-tert-alkylresorcinol is nitrated in one of two ways to form a 2-halo-4,6-dinitroresorcinol (IV), which is then hydrogenated to from the 4,6-diaminoresorcinol.

The invention also relates to a novel chemical composition-2-halo-4,6-di-tert-alkylresorcinol (III)—and a process for preparing same.

8 Claims, No Drawings

SYNTHESIS OF DIAMINORESORCINAL FROM RESORCINOL

BACKGROUND OF INVENTION

This invention relates to a process for preparing 4,6-diamino-1,3-benzenediol (4,6-diaminoresorcinol). More specifically, it relates to the synthesis of 4,6-diaminoresorcinol starting with 1,3-benzenediol (resorcinol).

Diaminoresorcinols are useful as monomers for the preparation of polybenzoxazoles (PBOs), the utility of which is discussed by, for example, Wolfe in Mark et al., "The Encyclopedia of Polymer Science and Engineering", vol. 11, pp. 601–635, Wiley-InterScience Publication, New York, 1988. One of the more efficient and economical methods of preparing 4,6-diaminoresorcinol had been Lysenko's process (U.S. Pat. No. 4,766,244, herein incorporated by reference) which reported the synthesis of the desired product in high purities and yields in three steps from 1,2,3-trichlorobenzene.

Unfortunately, halogenated organic compounds—including halogenated arenes—have become the subject of close environmental scrutiny in recent years. Consequently, the once inexpensive and plentiful 1,2,3-trichlorobenzene is becoming expensive and difficult to obtain. The questionable long-term availability of 1,2,3-trichlorobenzene requires that an inexpensive commodity starting material be found to prepare 4,6-diaminoresorcinol.

Lysenko et al. addresses this problem somewhat in U.S. Pat. No. 4,982,001, herein incorporated by reference, by preparing 4,6-diaminoresorcinol from the inexpensive and readily available resorcinol by way of a 1,3-bis(methylcarbonato)benzene intermediate. The steric hindrance of this intermediate causes nitration to take place mostly at the 4- and 6-positions, so that the desired 4,6-diaminoresorcinol can be prepared upon hydrolysis and hydrogenation. Unfortunately, a significant degree of undesirable nitration occurs at the 2-position of the intermediate, making this process impractical.

In view of the deficiencies in the art, it would be desirable to prepare 4,6-diaminoresorcinol from resorcinol by a process where undesirable nitration does not occur.

SUMMARY OF INVENTION

The invention is a process which comprises reacting a 4,6-di-tert-alkylresorcinol with a halogenating agent to make a 2-halo-4,6-di-tert-alkylresorcinol.

A further aspect of this invention is that it is a process for preparing 4,6-diaminoresorcinol from resorcinol which comprises the steps of:
  a) reacting resorcinol with a tert-alkylating agent to form a 4,6-di-tert-alkylresorcinol; then
  b) halogenating the 4,6-di-tert-alkylresorcinol to form a 2-halo-4,6-di-tert-alkylresorcinol; then
  c) nitrating the 2-halo-4,6-di-tert-alkylresorcinol to form a 2-halo-4,6-dinitroresorcinol; and then
  d) hydrogenating the 2-halo-4,6-dinitroresorcinol to form 4,6-diaminoresorcinol.

A further aspect of this invention is that it is a compound having the structure:

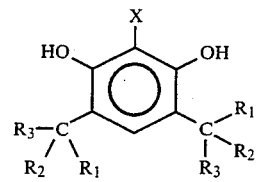

wherein $R_1$, $R_2$, and $R_3$, are each independently alkyl, aryl, arylalkyl, or cycloalkyl; and X is fluoro, chloro, bromo, or iodo.

A further aspect of this invention is that it is a process which comprises nitrating a 2-halo-4,6-di-tert-alkylresorcinol to form a 2-halo-4,6-dinitroresrocinol.

The present invention addresses the problems associated with 1,2,3-trichlorobenzene by preparing 4,6-diaminoresorcinol from resorcinol—an inexpensive, readily available, and environmentally acceptable alternative—and through a synthetic route heretofore unknown.

DETAILED DESCRIPTION OF INVENTION

In one aspect of this invention, 4,6-diaminoresorcinol is prepared from resorcinol as shown:

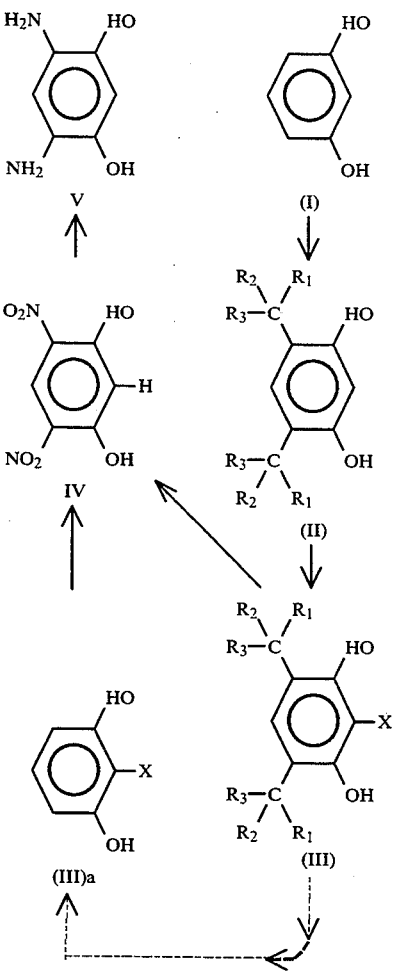

wherein $R_1$, $R_2$, and $R_3$ are each independently alkyl, aryl, heteroaryl, arylalkyl, or cycloalkyl; and X is fluoro, chloro, bromo, or iodo. Preferably, $R_1$, $R_2$, and $R_3$ are each independently alkyl, more preferably methyl. Preferably, X is chloro or bromo.

In the first step of the process, resorcinol (I) is reacted with a tertiary alkylating agent to form a 4,6-di-tert-alkylresorcinol (II). Then, the 4,6-di-tert-alkylresorcinol is reacted with a halogenating agent to form a 2-halo-4,6-di-tert-alkylresorcinol (III). The 2-halo-4,6-di-tert-alkylresorcinol is de-tert-alkylated and nitrated by one of two routes to form a 2-halo-4,6-dinitroresorcinol (IV). Finally, the 2-halo- 4,6-dinitroresorcinol is hydrogenated to form diaminoresorcinol (V).

Di-tert-alkylation and tertiary alkylating reagents

A tertiary alkylating agent is any agent that can be reacted with resorcinol under such conditions to form a 4,6-di-tert-alkylresorcinol (compound (II) in the scheme). Generally, suitable agents are those capable of forming tertiary alkyl carbocations. These agents include tertiary alcohols of the form $C(R_1R_2R_3)$—OH; tertiary-alkyl alkyl ethers of the form $C(R_1R_2R_3)$—O—R, or tertiary-alkyl aryl ethers of the form $C(R_1R_2R_3)$—O—Ar; tertiary alkyl halides of the form $C(R_1R_2R_3)$—X; gem-disubstituted alkenes of the form $C(R_1R_2)$=$CH_2$, trisubstituted alkenes of the form $C(R_1R_2)$=$CHR_3$, or tetrasubstituted alkenes of the form $C(R_1R_2)$=$C(R_3R_4)$; where $R_1$, $R_2$, $R_3$, and X are previously defined; R is an alkyl or cycloalkyl group; $R_4$ is alkyl, cycloalkyl, aryl, heteroaryl, or arylalkyl; and Ar is aryl or heteroaryl. The preferred tertiary alkylating agents are tertiary alcohols, tertiary-alkyl alkyl ethers, tertiary alkyl halides, and gem-disubstituted alkenes. The more preferred tertiary alkylating reagents are tert-butanol, tert-butyl methyl ether, tert-butyl chloride, and isobutene.

It is also possible for a tertiary carbocation to form through the rearrangement of a secondary carbocation. For example, the secondary alcohol 2-methylpentan-4-ol rearranges to form the more stable tertiary carbocation in the presence of an acid. (See Huston et al., *J. Am. Chem. Soc.*, 58, 439 (1936); and Schriesheim in Olah, "Friedel Crafts and Related Reactions," Volume II, Part 1, page 501, Interscience Publishers, New York, 1964.) Thus, a tertiary alkylating reagent may also be those secondary alkyl halides, monosubstituted alkenes, secondary alkyl alkyl ethers, secondary alkyl aryl ethers, or secondary alcohols, which can form tertiary carbocations. Examples of such compounds include 2-butyl chloride, cyclohexanol, 2-butyl methyl ether, and 3-methyl-1-butene.

The tertiary carbocation may also be formed through the rearrangement of a neopentyl ($(CH_3)_3CCH_2+$) or neophenyl ($PhC(CH_3)_2CH_2$) carbocation formed by the treatment of, for example, neopentyl or neophenyl bromide with an acid. (See March, "Advanced Organic Chemistry", Second Edition, pages 964 and 967, McGraw-Hill, Inc., New York, 1977.)

The tertiary alkylating reagents are almost always used in concert with an acid, preferably a catalytic amount of acid. The acid may be either a metal halide type Lewis acid, such as $AlCl_3$, or a protic acid, such as sulfuric acid. However, certain tert-alkylation reactions occur without catalyst. For example, triphenylmethyl chloride alkylates resorcinol without a catalyst. (See Hart et al., *J. Am. Chem. Soc.*, 76, 1634 (1954), herein incorporated by reference.)

Theoretically, 2 mole equivalents of the tertiary alkylating reagent are needed per mole equivalent of the resorcinol to form the di-tert-alkylresorcinol. In practice, excess of 2 mole equivalents of the tertiary alkylating agent is used, though the degree of the excess does not appear to be critical. In an example of a tertiary alkylation reaction, about 3 to about 5 mole equivalents of a tertiary alkylating reagent, preferably a tert-butylating reagent, are reacted with about 1 mole equivalent of resorcinol in the presence of a catalytic amount of acid, preferably sulfuric acid, preferably between about 0.01 and 0.5 mole equivalents, at a temperature ranging from about 20° C. and 100° C., preferably ranging from about 20° C. and 50° C., until the reaction is substantially complete, preferably for between about 10 minutes and about 5 hours, more preferably for between 30 minutes and 2 hours.

The 4,6-di-tert-alkylresorcinol can be isolated by, for example, extraction with an organic solvent which substantially dissolves organics, but which is substantially insoluble with inorganics, such as methylene chloride. However, the 4,6-di-tert-alkylresorcinol is advantageously used in the next step of the series of reactions without being isolated. The preferred 4,6-di-tert-alkylresorcinol, 4,6-di-tert-butylresorcinol, is a commercially available compound.

Halogenation of 4,6-di-tert-alkylresorcinol

The 4,6-di-tert-alkylresorcinol is reacted with a halogenating agent to form a 2-halo-4,6-di-tert-alkylated resorcinol. Any halogenating agent that adds a halo group to a phenolic compound may be used. The halogenating agents may be fluorine, chlorine, bromine, and iodine; preferably bromine and chlorine; and more preferably chlorine.

It is preferable to chlorinate or brominate the 4,6-di-tert-alkylresorcinol using free halogens in nonaqueous solvents that do not react with the halogens. Suitable solvents include, but are not restricted to alcohols, such as methanol or ethanol; organic acids, such as acetic acid; chlorinated organic solvents, such as carbon tetrachloride and methylene chloride; or mixtures thereof. The reaction is preferably carried out at temperatures less than 30° C., more preferably between about 5° C. and about 25° C.

Reagents that easily liberate chlorine or bromine in situ, such as a dilute hydrogen halide and an oxidizing reagent in an aqueous medium are also suitable. For example, a mixture of dilute hydrochloric acid and an aqueous solution of an alkaline chlorate favor chlorine liberation, and a mixture of dilute hydrobromic acid and an aqueous solution of an alkaline bromate favor bromine liberation. The preferred concentration of aqueous dilute hydrogen halide is between about 5% and about 25% v/v. The preferred temperature range is between about −5° C. and about 25° C.

The preferred 2-halo-4,6-di-tert-alkylresorcinol is 2-chloro-4,6-di-tert-butylresorcinol or 2-bromo-4,6-di-tert-butylresorcinol, more preferably 2-chloro-4,6-di-tert-butylresorcinol.

Nitration of 2-halo-4,6-di-tert-alkylresorcinol

The 2-halo-4,6-di-tert-alkylresorcinol is converted to a 2-halo-4,6-dinitroresorcinol through protodealkylation followed by nitration. The intermediate protodealkylated species, 2-haloresorcinol (IIIa in the scheme), can be isolated, but the 2-halo-4,6-di-tert-alkylresorcinol is preferably converted to the 2-halo-4,6-dinitroresorcinol directly, without isolating the 2-haloresorcinol.

The conversion of both the 2-halo-4,6-di-tert-alkylresorcinol and the 2-haloresorcinol to the 2-halo-4,6-dinitroresorcinol are carried out in substantially the same manner. For the purposes of this discussion, haloresorcinol refers to either the 2-halo-4,6-di-tert-alkylresorcinol or the 2-haloresorcinol.

Generally, any nitrating agent which will nitrate haloresorcinol at the 4- and 6-positions under the reaction conditions described herein can be used. Suitable nitrating agents include alkali metal nitrates, such as sodium and potassium nitrate; and nitric acid at various concentrations, such as fuming nitric acid and concentrated nitric acids. Concentrated nitric acid, e.g., from about 60 to about 75 weight percent nitric acid, especially about 70 weight percent, is the most preferred nitrating agent.

Any ancillary acid which, in the presence of nitric acid, will facilitate the formation of nitronium ions under the reaction conditions described herein can be used in the nitration step of the present process. Suitable ancillary acids for this purpose include trifluoroacetic acid, acetic acid, hydrochloric acid, and sulfuric acid.

Suitable molar ratios of nitrating agent to haloresorcinol are those sufficient to cause the substitution of 2 nitro groups per molecule of haloresorcinol. The nitrating agent is generally used in stoichiometric excess, though the degree of excess does not appear to be critical. Typical molar ratios of ancillary acid, preferably sulfuric acid or acetic acid, to the haloresorcinols are in the range from about 8:1 to about 25:1, with about 10:1 to about 20:1 being more preferred.

The nitration of haloresorcinol is found to be quite rapid, probably because the hydroxy groups of these compounds are strong promoters of electrophilic aromatic substitution. Consequently, it is advantageous to control the temperature of the nitration reaction and the rate of addition of the nitrating reagent to minimize the formation of undesirable byproducts. In a preferred embodiment of the nitration of haloresorcinol, a mixture of nitric acid and acetic acid is added to a homogeneous mixture of 2-chlororesorcinol-4,6-disulfonic acid and acetic acid at a rate appropriate to control the resultant exotherm, and to minimize the formation of side products. The temperature of this reaction is preferably between about $-10°$ C. and about $20°$ C., more preferably between about $0°$ C. and about $15°$ C. The pressure of the nitration step can be any pressure at which nitration will occur. Preferred pressures are about atmospheric, although subatmospheric or superatmospheric pressures can be employed.

The 2-halo-4,6-dinitroresorcinol produced by this step can be isolated by conventional precipitation and filtration techniques and is typically obtained in greater than 95 percent purity, preferably greater than 98 percent purity and most preferably greater than about 99.9 percent purity.

If desired, this compound may be further purified by means such as recrystallization from an appropriate solvent, such as ethanol. However, the 2-halo-4,6-dinitroresorcinol can generally be used in the hydrogenation step of the present invention without further purification.

Hydrogenation of 2-halo-4,6-dinitroresorcinol

The hydrogenation step of the present invention involves contacting the 4,6-dinitro-2-haloresorcinol with a hydrogenating agent. The hydrogenating agent can be any material which will supply hydrogen to the reaction. Suitable hydrogenating agents include hydride reducing agents, such as lithium aluminum hydride; dissolving metal reducing agents in protic solvents, such as sodium amalgam in ethanol; and hydrogen over a catalyst. Of the hydrogenating agents, hydrogen over a catalyst is preferred. More preferably, the reduction step involves contacting the 4,6-dinitro-2-haloresorcinol with hydrogen over a catalyst in the presence of a solvent.

The solvent is one that remains unreactive under the hydrogenation conditions. Suitable solvents include alcohols, such as ethanol, methanol and propanol; alkylene glycols, such as ethylene glycol; and carboxylic acids, such as acetic acid, with carboxylic acids being preferred. The preferred carboxylic acid is acetic acid.

Useful hydrogenation catalysts include materials that contain a noble metal and will catalyze the reduction of the nitro groups of and the elimination of the halogen from the 2-halo-4,6-dinitroresorcinol. Examples of suitable catalysts include noble metals on carbon, noble metal oxides and noble metals supported on alkaline earth carbonates. Noble metals herein refer to gold, silver, platinum, palladium, iridium, rhodium, mercury, ruthenium and osmium. Preferred catalysts include palladium-on-carbon, platinum-on-carbon and platinum oxide.

The catalyst is used in an amount sufficient to catalyze the conversion of starting material in the presence of a hydrogenating agent to the corresponding diaminoresorcinol. Typically, from about 0.001 to about 1 molar equivalents of catalyst per equivalent of the initial concentration 2-halo-4,6-dinitroresorcinol are used. Preferably, from about 0.01 to about 0.5 and more preferably from about 0.01 to about 0.1 molar equivalents of the initial concentration of 2-halo-4,6-dinitroresorcinol are used.

Suitable concentrations of 2-halo-4,6-dinitroresorcinol in the reaction medium are those sufficient to afford an efficient recovery of product. Examples of such suitable concentrations are those in the range from about 0.001 to about 10 molar, with from about 0.01 to about 5 molar being preferred.

The amount of hydrogenating agent used in the reduction step is an amount sufficient to convert 2-halo-4,6-dinitroresorcinol to 4,6-diaminoresorcinol. In general, a large excess of the hydrogenating agent is used to enhance the reaction rate. Suitable amounts include those in the range from about 200 to about 2000 mole percent based on moles of the 2-halo-4,6-dinitroresorcinol, and preferably from about 500 to about 1000 mole percent. The temperature in the hydrogenation step is sufficient to effect completion of the hydrogenation reaction. Preferably, the temperature is in the range from about $0°$ C. to about $150°$ C., more preferably from about $30°$ C. to about $75°$ C. Pressures employed are suitably from about 1000 psi to about 1 psi, more preferably from about 400 psi to about 2 psi.

The 4,6-diaminoresorcinol can be recovered using known recovery methods such as precipitation and filtration. The product is generally isolated and stored as a hydrohalide salt advantageously mixed with an antioxidant, such as $SnCl_2$, to prevent oxidative decomposition. It is also common practice to isolate the product as a salt of a mineral acid such as sulfuric, nitric, or phosphoric acid. The 4,6-diaminoresorcinol of the present invention is typically obtained in a purity greater than 98 weight percent, preferably greater than 99 weight percent, most preferably greater than 99.9 weight percent, with yields being typically greater than 80 mole percent, preferably greater than 85 mole percent and most preferably greater than 95 mole percent, based on moles of the 2-halo-4,6-dinitroresorcinol charged to the reaction.

The 4,6-diaminoresorcinol is used to make polybisbenzoxazoles (PBOs), polymers which can be used in applications such as insulators, solar arrays, and tear-resistant gloves. ( See Wolfe, supra. )

Example 1

A. Preparation of 2-Chloro-4,6-di-tert-butylresorcinol from 4,6-Di-tert-butylresorcinol To a solution of 4,6-di-tert-butylresorcinol (2.2 g, 10 mmol) in methanol (20 mL) is added a solution of $Cl_2$ (1 g, 1.4 mmol) in methanol (10 mL) over a ten minute period. The mixture is stirred at room temperature for one hour. Evaporation of the solvent affords the crude product, which is purified by recrystallization from hexane, to give 2.1 g (82% yield) of the pure product.

B. Preparation of 2-Chloro-4,6-dinitroresorcinol from 2-Chloro-4,6-di-tert-butylresorcinol A stirred solution of 2-chloro-4,6-di-tert-butylresorcinol (2.6 g, 10 mmol) in glacial acetic acid (5 mL) is treated at 0° C. with a mixture of $HNO_3$ (70%; 10 mL) and glacial acetic acid (7 mL). After 0.5 hours, the mixture is poured into ice-cold water (20 mL) with stirring, and the solid that separates is collected by filtration. Recrystallization from ethanol-$H_2O$ affords 1.8–1.9 g (77–81% yield) of pure 2-chloro-4,6-dinitroresorcinol. This compound is used to prepare 4,6-diaminoresorcinol dihydrochloride.

C. Large Scale Preparation of 4,6-Diaminoresorcinol Dihydrochloride from 2-Chloro-4,6-dinitroresorcinol A one-liter Hastalloy C autoclave equipped with a gas dispersion stirrer and cooling coil is charged with 117.3 g (0.5 mole) of 2-chloro-4,6-dinitroresorcinol, 400 ml of glacial acetic acid, 41 g (0.5 mole) of NaOAc, 7.0 g of 10 percent palladium over carbon and 100 mL of $H_2O$. The sealed reactor is charged with 400 psi of $H_2$ and the temperature is brought to 40° C. and maintained between 40° C. and 50° C. during the course of the reaction. After a brief induction period, the uptake of hydrogen becomes extremely rapid and $H_2$ pressure is maintained between 100–400 psi during the reaction. Upon completion, no further uptake of $H_2$ is observed. The reactor is cooled to room temperature, opened and 400 mL of concentrated HCl containing 10 g of $SnCl_2 \cdot 2H_2O$ is added to the reaction mixture. The crude product with the catalyst is isolated by filtration. This material is dissolved in 200 g of $H_2O$ at 85° C. and the catalyst is removed by filtration. $H_2$ (100–300 mL) is added to the filtrate along with 500 mL of HCl and the catalyst-free material is precipitated from the brown solution. Recrystallization is carried out in the existing solvent or the semi-pure material can be isolated and air dried to afford 100 g of crude diaminoresorcinol dihydrochloride, (96.8 mole percent yield based on the 2-chloro-4,6-dinitroresorcinol.

Example 2

A. Preparation of 2-Chlororesorcinol from 2-Chloro-4,6-di-tert-butylresorcinol A mixture of 2-chloro-4,6-di-tert-butylresorcinol (25.7 g, 100 mmol, prepared as described in Example 1A) and p-toluenesulfonic acid monohydrate (0.2 g, 1 mmol) is added to a flask—which is equipped with a gas withdrawing port leading to a dry ice cooled trap—heated at 210° C. for 2 hours, then allowed to cool. Recrystallization from toluene affords pure 2-chlororesorcinol (13.2–13.9 g, 91–96% yield). The yield of recovered isobutylene is >95%.

B. Preparation of 2-chloro-4,6-dinitroresorcinol from 2-Chlororesorcinol

2-Chlororesorcinol (0.36 g, 2.5 mmol) is placed in a flask which is chilled in an ice-water bath. Concentrated sulfuric acid (5 g) is added slowly with stirring so as not to allow the mixture to warm up. After the 2-chlororesorcinol is dissolved, a premixed solution of $HNO_3$ (70%, 0.9 g, 10 mmol) in concentrated sulfuric acid (5 g) is added dropwise with rapid stirring at such a rate that the temperature does not exceed 15° C. After 20 minutes, the mixture is carefully poured into ice-water (30 mL) with stirring. The solid that separates is collected by filtration and washed with water. Air drying affords 2-chloro-4,6-dinitroresorcinol in sufficient purity—as determined by high performance liquid chromatography, gas chromatography-mass spectrometry, and proton and carbon NMR spectroscopy—that further purification is not needed. The yield is 65%.

What is claimed is:

1. A process for preparing diaminoresorcinol which comprises the steps of:
   a) tert-alkylating resorcinol to form a 4,6-di-tert-alkylresorcinol; then
   b) halogenating the 4,6-di-tert-alkylresorcinol to form a 2-halo-4,6-di-tert-alkylresorcinol; then
   c) nitrating the 2-halo-4,6-di-tert-alkylresorcinol to form a 2-halo-4,6-dinitroresorcinol; then
   d) hydrogenating the 2-halo-4,6-dinitroresorcinol to form 4,6-diaminoresorcinol.

2. The process of claim 1 wherein the 4,6-di-tert-alkylresorcinol is 4,6-di-tert-butylresorcinol.

3. The process of claim 1 wherein the halogenating agent is chlorine.

4. The process of claim 1 wherein the nitrating agent comprises a mixture of nitric acid and acetic acid.

5. The process of claim 1 wherein the tert-alkylating agent is a tert-alkanol, a gem dialkyl substituted alkene, a trialkyl substituted alkene, a tetraalkyl substituted alkene, a tert-alkyl chloride, a tert-alkyl alkyl ether, or a tert-alkyl aryl ether.

6. The process of calim 5 wherein the tert-alkylating reagent is a tert-alkyl alkyl ether.

7. The process of claim 6 wherein the tert-alkyl alkyl ether is tert-butyl methyl ether.

8. The process of claim 1 wherein the hydrogenating agent is hydrogen over a catalyst.

* * * * *

UNITED STATES PATENT AND TRADEMARK OFFICE
CERTIFICATE OF CORRECTION

PATENT NO. : 5,410,083
DATED : April 25, 1995
INVENTOR(S) : Bassam S. Nader

It is certified that error appears in the above-indentified patent and that said Letters Patent is hereby corrected as shown below:

Title page, item [54], line 1, and col. 1, line 1 should read as follows:
--DIAMINORESORCINOL --.

Signed and Sealed this

Twelfth Day of March, 1996

Attest:

BRUCE LEHMAN

Attesting Officer

Commissioner of Patents and Trademarks